United States Patent [19]
Hickok et al.

[11] Patent Number: 5,868,570
[45] Date of Patent: Feb. 9, 1999

[54] ULTRASONIC DENTAL TOOL

[75] Inventors: Teresa R. Hickok, Bonita; Claude E. Martin, Chula Vista; Clifford J. Ruddle, Santa Barbara, all of Calif.

[73] Assignee: San Diego Swiss Machining, Inc., Chula Vista, Calif.

[21] Appl. No.: 766,787

[22] Filed: Dec. 13, 1996

[51] Int. Cl.$^6$ ...................................................... A61C 5/02
[52] U.S. Cl. ......................... 433/102; 433/119; 433/224
[58] Field of Search .................................. 433/102, 119, 433/165, 166, 224

[56] References Cited

U.S. PATENT DOCUMENTS

| | | | |
|---|---|---|---|
| 4,019,254 | 4/1977 | Malmin | 433/102 |
| 4,135,302 | 1/1979 | Kronman et al. | 433/102 |
| 4,609,352 | 9/1986 | Riitano | 433/102 |
| 4,981,756 | 1/1991 | Rhandhawa | 428/336 |
| 5,026,284 | 6/1991 | Martin | 433/102 |
| 5,094,617 | 3/1992 | Carr | 433/119 |
| 5,100,321 | 3/1992 | Coss et al. | 433/118 |
| 5,145,739 | 9/1992 | Sarin | 428/336 |
| 5,242,302 | 9/1993 | Riehm | 433/164 |
| 5,266,389 | 11/1993 | Omori et al. | 428/216 |
| 5,320,530 | 6/1994 | Fong | 433/119 |
| 5,330,481 | 7/1994 | Hood et al. | 606/99 |
| 5,376,444 | 12/1994 | Grotepass et al. | 428/336 |
| 5,489,208 | 2/1996 | Mandell | 433/165 |
| 5,490,779 | 2/1996 | Malmin | 433/81 |
| 5,540,587 | 7/1996 | Malmin | 433/81 |
| 5,567,153 | 10/1996 | Foulkes et al. | 433/119 |

FOREIGN PATENT DOCUMENTS

| | | |
|---|---|---|
| 3327535 A1 | 2/1985 | Germany . |
| WO 86/05967 | 10/1986 | WIPO . |

*Primary Examiner*—John J. Wilson
*Attorney, Agent, or Firm*—Baker & Maxham

[57] ABSTRACT

An ultrasonic dental tool for use with an ultrasonic transducer, comprises a substantially elongate tool defined by a shaft having a proximal end with a connector for attachment to an ultrasonic transducer, a distal end having a tip configured for performing a dental procedure, a portion of straight cylindrical wall from the tip inward toward the proximal end, and a contra-angle portion of substantially uniform diameter on the proximal end, and a uniform gradual tapered portion intermediate the distal end and the proximal end.

25 Claims, 3 Drawing Sheets

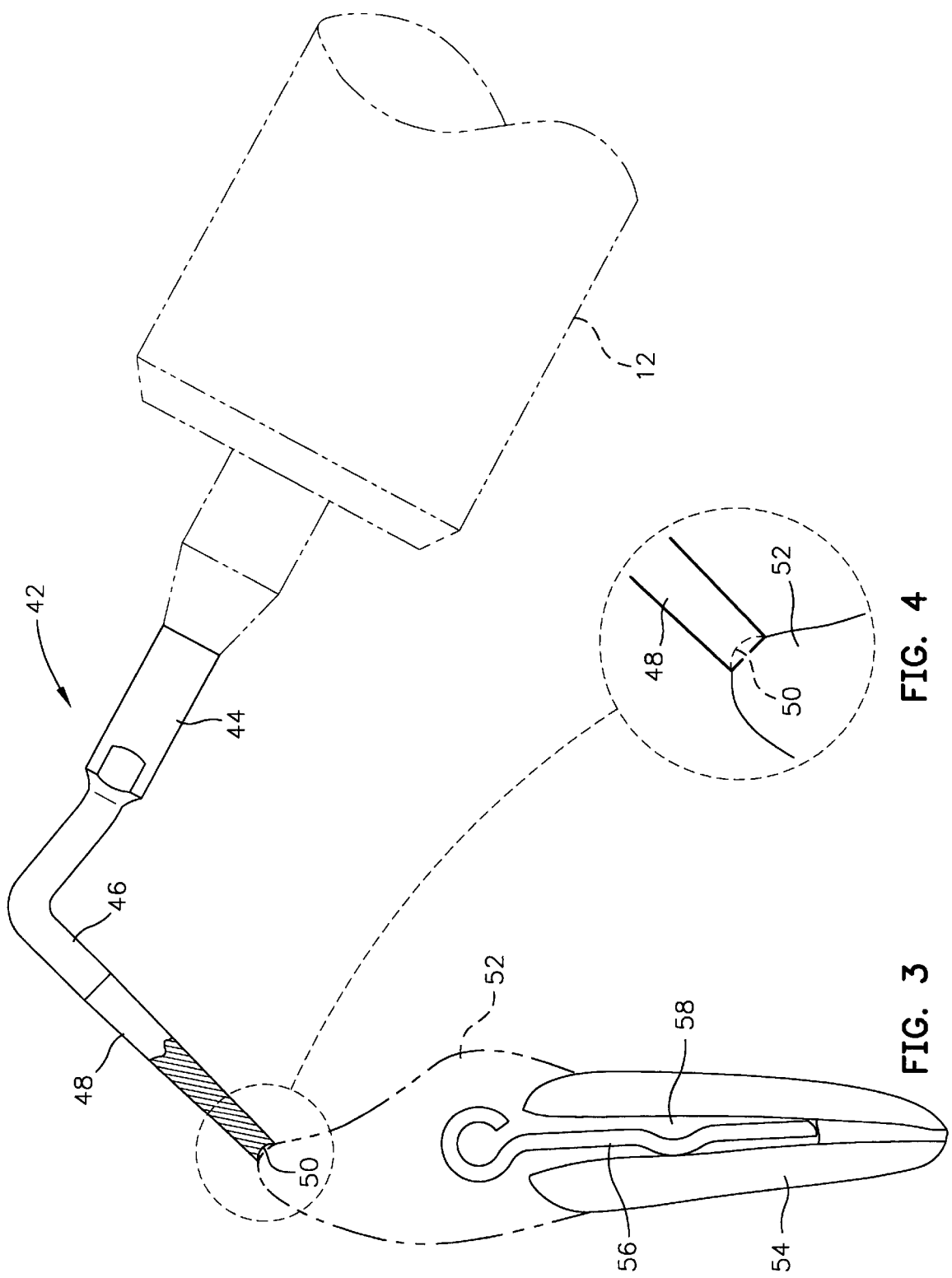

ULTRASONIC DENTAL TOOL

BACKGROUND

This invention relates generally to ultrasonic dental tools and more specifically to special non-surgical ultrasonic root canal tools.

Dental surgeons commonly use a tool usually called a tip coupled to an ultrasonic generator for operations on teeth, bones, and soft tissue including dislodging and removal of dental material. The use of ultrasonic generators for powering tools for clinical dentistry has been widely used in virtually all areas, except for root canal. Root canal work until recently has been largely limited to manual instruments for various reasons. One of the main reasons is the difficulty of providing tools that can be powered by ultrasonic generators that also provide access of the tool for precision root canal work. For this reason, such tools in the past have been largely limited to manually manipulated tools and instruments, such as disclosed for example, in U.S. Pat. No. 5,026,284 issued Jun. 25, 1991 to Martin. As expressed in the background of that patent, the success of root a canal depends upon very precise and controlled preparation and shaping of the root canal.

A properly shaped root canal presents a gradually tapering cone with the narrowest part directed apically. A typical root canal is prepared by mechanical instruments used to enlarge the root canal by physically removing internal root canal tooth structure, dentin, by rotational cutting or abrasive action. These tools are tapered and pointed metal instruments with cutting edges so that the cutting occurs either on a push or pull of the stroke. With these instruments the dentist through hand manipulation prepares the canal for precise filling. The object of the preparation is to attain an apical terminus kept as small as practical in order to achieve more effective packing with greater control upon an effectively prepared seat.

Recent years have seen the proposed use of ultrasonically powered instruments for the preparation of root canals. Examples of instruments of this type are disclosed in U.S. Pat. No. 4,019,254, issued Apr. 26, 1977 to Malmin, U.S. Pat. No. 5,094,617 issued Mar. 10, 1992 to Carr and PCT Publication WO 86/05967. With the exception of the first mentioned patent, all tools are formed with a shaft tapered to a point. In the preparation of root canals, it has been found that tapered tools plug and obstructs the view of the canal wall operation from the crown area. Also, they are difficult to operate with an ultrasonic generator and provide access to remote or posterior teeth in the mouth.

The instruments of the Malmin patent are disclosed and designed for selective positioning of abrasive materials to eliminate cutting edges and thereby eliminate the need for tempering the instruments. This construction reportedly provides greater adaptability to eliminate breakage of the tools. However, it fails to provide configurations enabling it to be used with ultrasonic power units in remote or posterior areas of the mouth. In addition, it fails to provide a construction enabling the viewing of the area of cutting in the root canal.

Therefore, there is a need for an improved ultrasonic dental tool for enabling the effective root canal preparation from the crown area of the tooth.

SUMMARY OF THE INVENTION

A primary objective of this invention is to provide an improved ultrasonic dental non-surgical tool having a tip that is shaped to provide improved procedural access.

Another objective is to provide a tool that can be made small enough for microendodontics. In accordance with a primary aspect of the present invention a dental tool for use with an ultrasonic transducer comprises a substantially elongate tool defined by a shaft having a proximal end with means for attachment to an ultrasonic transducer, and a distal end having a tip configured for performing a dental procedure, an intermediate contra-angle portion, and a portion of straight cylindrical configuration from said tip inward toward said proximal end.

BRIEF DESCRIPTION OF DRAWING

The objects, advantages and features of this invention will be more readily appreciated from the following detailed description, when read in conjunction with the accompanying drawing, in which:

FIG. 3 is an side elevation view of another embodiment of an ultrasonic dental tool shown in use; and FIG. 4 is an enlarged detailed view of the tool of FIG. 3.

DETAILED DESCRIPTION OF PREFERRED EMBODIMENTS

Figure 1:
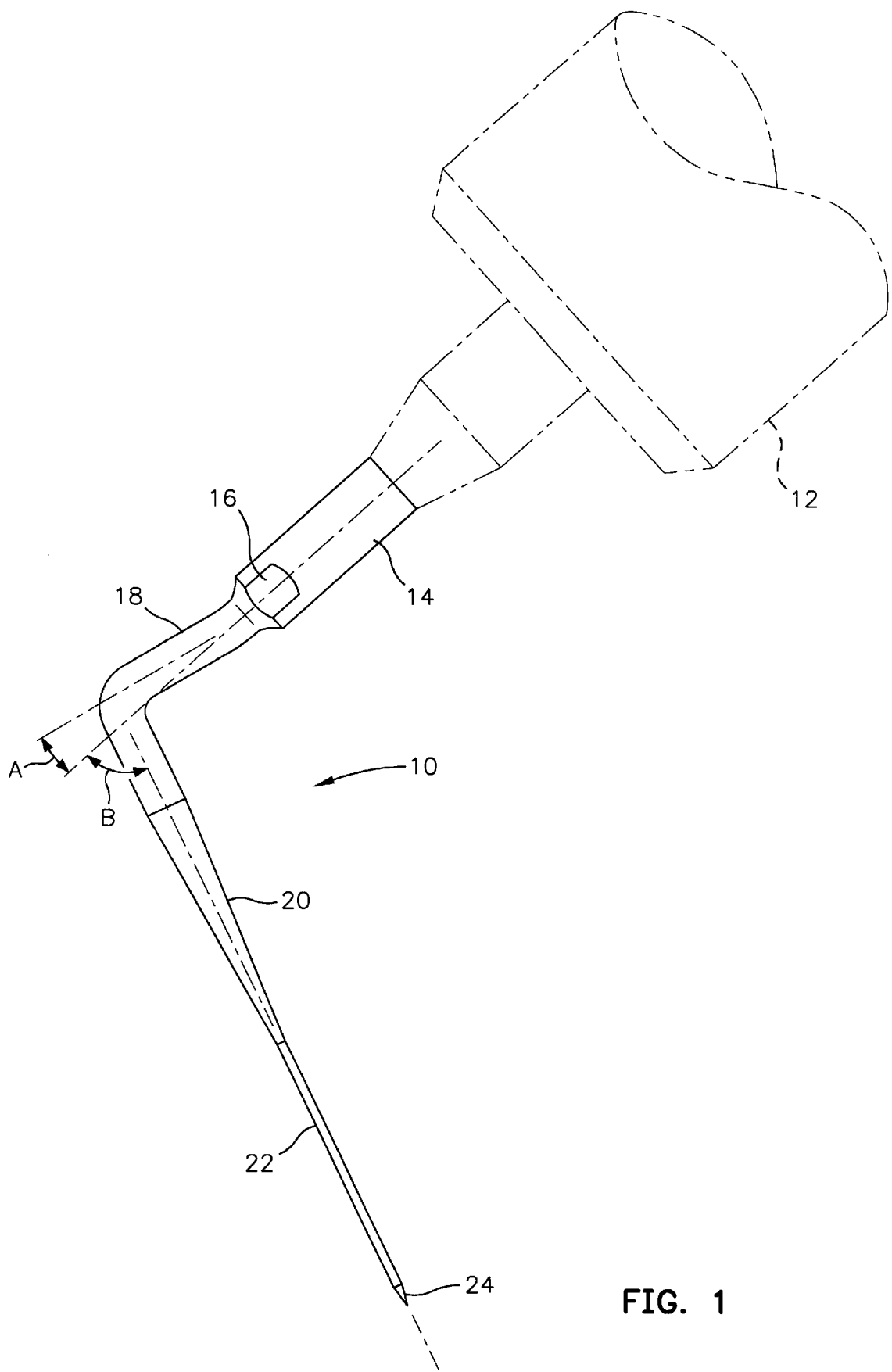
FIG. 1 is a side elevation view of an ultrasonic dental tool constructed in accordance with a preferred embodiment of the invention.

The present invention is described with reference to a preferred embodiment of the invention as illustrated in the drawings. While this invention is described in terms of the best mode for achieving this invention's objectives, it will be appreciated by those skilled in the art that variations may be made in view of these teachings without deviating from the spirit or scope of the invention.

Referring to FIG. 1 of the drawings there is illustrated an exemplary embodiment of a tool for dental preparations, in accordance with the present invention, designated generally by the numeral 10. The tool is shown connected to an ultrasonic vibrator or transducer 12 (shown in phantom) of generally well-known conventional construction. The tool, as illustrated, comprises an elongated shank having connecting means 14 at a proximal end. The connection means in shown in the form of a threaded socket for threadably mounting on the end of a shaft and having a flat 16 for engagement by a wrench or the like for threadably tightening and loosening the tool.

The tool has a proximal end portion 18 which is curved to form what is commonly called a contra-angle. This contra-angle portion is curved or bent in a first direction away from the axis of the proximal end at an angle A of about 15°–25°, extending away from the proximal end. This contra-angle portion then curves or bends back across the axis of the proximal end or connection means at an angle B of about 45° or about 70° to the axis of the connecting means.

The proximal portion 18 extends outward from the connecting collar 14 and is of a generally uniform diameter with the contra-angle curved in a manner, as illustrated. An intermediate portion or section 20 of the shaft tapers gradually down to a distal or working end portion 22, having a generally uniform cylindrical configuration extending from the intermediate portion 20 outward to a tip 24 which may have a sharpened point or other form. This portion 22 is the primary working portion and may have a length of from about 0.25 to about 0.394 inches or six to about ten or twelve (6–10/12) mm. This portion has a diameter of about 0.015 to about 0.0250 inches or about 0.4 to 0.6 mm.

The typical tool will come in sets of, for example, three tools with a first having an end of about 0.25 inches or 6 mm in length and about 0.0250 inches or about 0.6 mm in diameter for working in the coronal aspect of the tooth from the crown area. This is designed for performing non-surgical root canal through a crown opening. A medium sub-orifice tip or tool will be provided in the range of about 5 mm in length and a diameter of about 0.6 mm in diameter for working in the medial aspect of the root while performing non-surgical root canal work at this point through the crown opening. Finally, a long sub-orifice tip of about 10 mm and about 0.4/0.5 mm in diameter is provided for working in the apical aspect or area of the root while performing root canal work.

Figures 2, 2A:
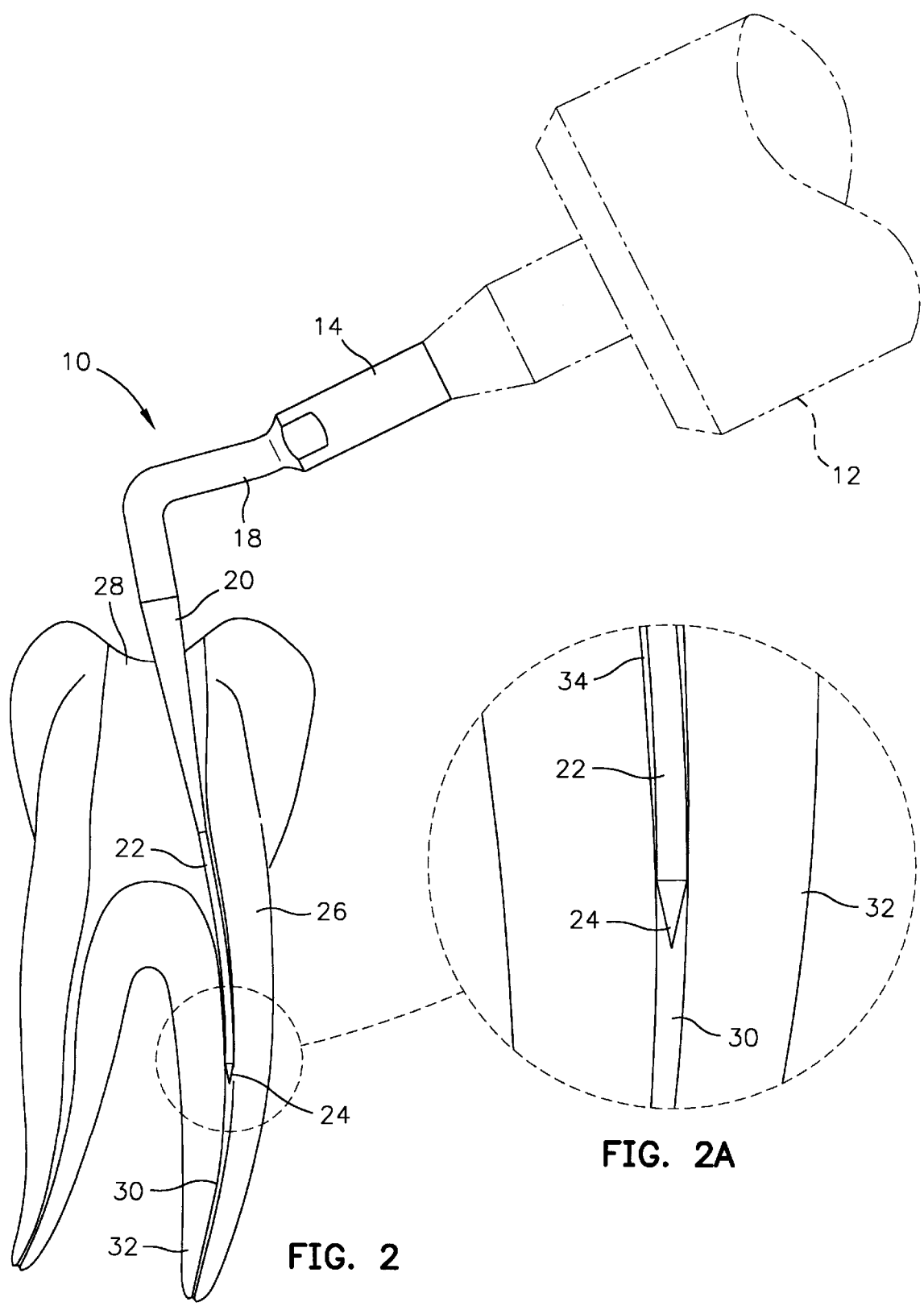
FIG. 2 is a view like FIG. 1 showing the tool in a root canal in a tooth.
FIG. 2a is an enlarged detailed view of the tip of the tool as shown in FIG. 2.

Referring to FIGS. 2 and 2A, the tool is designed to use in the preparation of tooth root canals. As illustrated, the tool is shown in use in a canal of a tooth 26 having an opening 28 in the crown of the tooth. The tool is inserted through the opening 28 and into a canal 30 of a root 32 of the tooth. As can be seen in FIG. 2A, the working distal end 22 of the tool is of a uniform cylindrical diameter throughout its length, such that when positioned in the tapered root canal 30, it provides space 34 around the shaft to enable the operator to view or see the wall area surrounding the tool as it's performing its work. This cylindrical shape doesn't wedge in the canal as does the tapered tool of the prior art. It also gives debris room (space 34) to move out of the canal.

The size and configuration of the tool, with its gradual divergence at 20 from minimum diameter at the distal end portion 22 to maximum diameter at the proximal end portion 18, provides a strong rigid construction that reduces the possibility of breakage of the tool during use. The tool is also hardened and tempered or coated, as will be further explained to further strengthen it for its utility.

The tool is shaped with a contra-angle, as discussed above, wherein it curves first to one side of the axis and then extends across at an angle to the other side of the axis where the distal point is located. This angle provides better access to posterior areas of the mouth of the patient. This configuration has been utilized in hand tools for dental work, but has not been utilized in the ultrasonic tools.

The present invention provides instruments that, because of the critical characteristics, allow them to work predictably, safely, and efficiently to all teeth within the dentition. The double bent shaft, known as a contra-angle, enables dramatic improvement in procedural access. This configuration is unique to endodontic non-surgical ultrasonic instruments and allows them to work in the posterior teeth, as well as the anterior teeth. The most distal aspect of the ultrasonic instruments have been designed with up to 10 mm of parallelism, that is uniform diameter cylindrical portion then progressively, rather than abruptly, tapers toward the proximal end of the contra-angle. This feature allows massive improvement in vision when the instrument is placed inside a canal. Parallel sided (i.e. cylindrical) ultrasonic instruments allow for improved vision with loupes, magnification glasses or the operating microscopes when looking deep between the walls of the canal and the introduced ultrasonic instrument. Over the length of the instrument, a smooth transition from parallel sidewalls to progressive taper enhances strength and instrument activity while economically reducing expensive tip breakage, as evidenced in clinical trials.

The instruments may also be coated, as will be described, which provides a longer useful clinical life by reducing instrument breakage. It also produces more measurable energy, as compared to prior art and enhances performance in non-surgical endodontic treatments. The coating creates an abrasive which allows for tooth and efficient side and/or end cutting. The special coating eliminates chipping, gouging and potential dental burning, noted with tools according to the prior art.

The contra-angled head and designed shape provides enhanced energy for the successful removal of built-ups and pulp chamber cores. In addition, the instrument is excellent for chasing calcified canals, uncovering hidden orifices, troughing and obstructions located within the pulp chamber or extended below the surface.

These uniquely configured instruments afford significant visual advantages, as their design and progressively smaller profiles allow them to work in the coronal, middle, and apical ⅓'s of virtually all roots of all teeth. Its unsurpassed energy makes them ideal for eliminating broken instruments, chasing calcified canals and negotiating iatrogenic blocks.

The instruments are designed without a water port which are deemed unnecessary in this design, as well as undesirable. Flowing water creates airborne mists which can carry bacteria. In addition, flowing water obstructs the vision, which is so critical to effective utilization of the instruments.

Referring to FIGS. 3 and 4, an alternate tool, designated generally by the numeral 42, is illustrated having the same overall contra-angle configuration as that of FIG. 1, but with a concave point or tip 50. The tool has a connector socket 44 with a contra-angle portion 46 and a tapered portion 48 and concave tip 50. This tool or instrument was conceived and designed to efficiently apply energy to the removal of crowns, bridges, posts and other materials. The tool with its concave tip 50 dramatically improves energy, clinical applications and efficiency when removing crowns, bridges, posts and other restorative materials. This concave shape in this instrument is unique as it allows more intimate contact and transference of ultrasonic energy to the obstruction, such as posts, crowns, epoxies and cements and restorative materials.

As illustrated in FIG. 3, the tool is applied to a crown 52 (shown in phantom) which is mounted on a portion of a tooth 54 by means of a post 56 cemented into a bore 58 of the tooth. As shown in detail in FIG. 4, the concave shape tip of this instrument provides a more intimate contact and transference of ultrasonic energy to the tooth crown or other obstruction.

The instruments may, as mentioned above, be coated, such as disclosed in co-pending application Ser. No. 08/546,336 filed Oct. 20, 1995 and entitled "Hardening Process for Ultrasonic Dental Tips", now U.S. Pat. No. 5,704,787. One preferred coating is metal nitride. The metal nitride can be applied very thinly and still imparts excellent hardness properties in contrast to the relatively thick diamond coatings of the prior art that are required to gain hardness. The thin coating is desirable because the tips do not have to support the weight of the diamond abrasive, allowing for smaller diameter tips. Additionally, the small size allows the tip to access hard to reach areas that were not reachable with prior art tips. The small size also allows for a less intrusive invasion of the subject, for example, a smaller filling may be added to a tooth. The metal coating is preferably applied over the entire tool with the exception of threads.

In general, the preferred overall process for creating the tips is as follows. An ultrasonic dental tip is manufactured, bent into the proper shape, and roughened by an externally applied abrasive process. Then, a metal nitride coating is applied to the roughened outer surface. Preferably, the metal element is selected from the group consisting of Zirconium (Zr) and Titanium (Ti). Between a Ti-N and Zr-N coating, the latter is the hardest at about 3000 Vickers while the former is about 2800 Vickers. Either is harder than carbide instruments which are commonly used in the prior art, but softer than an instrument prepared with expensive diamond abrasives. However, either metal nitride provides a very hard surface tip with far less cost than those using diamonds. Further, one can expect long wear from tips created by the process of this invention because Ti-N and Zr-N are both highly resistant to abrasion and corrosion. Zr-N has not been used as a hard coating for surgical tips prior to this invention. This invention is based to an extent on the inventors critical recognition of its desirable properties.

Preferably, the tip is comprised of a metal substrate, such as stainless steel, and in particular the inventors have recognized that ASTM 13-8 stainless steel is a good choice for the substrate. It has been further recognized by the inventors that it is beneficial to heat treat the steel after the roughing step to achieve a Rockwell-C hardness rating of about 40–42. Heat treating is a well known process that involves heating and cooling of a metal in the solid state for the purpose of obtaining certain desirable properties including increased hardness.

One of the benefits of using stainless steel is that it is easy to heat treat. Empirical evidence shows that good results can be obtained by subjecting 13-8 stainless steel to a temperature of about 900° for about two hours.

When the roughing and heat treating is followed by the application of a metal nitride coating the result is an extremely hard tip having very desirable cutting abilities. The coating may be applied by any well-known technique in the art. While not desiring to be limited to any particular method of coating, the inventors have discovered that the well-known technique of using physical vapor deposition equipment employing cathodic arc techniques is a satisfactory way to deposit thin films of the metal nitrides on dental surgical tips. The coating is preferably applied very thinly so that its average thickness is about 0.0002 inches. An advantage of such a thin coating is that very small diameter tips can be created that are extremely hard and yet abrasive. Such small diameter tips are desirable in microendodontic procedures.

While we have illustrated and described our invention by means of specific embodiments, it is to be understood that numerous changes and modifications may be made therein without departing from the spirit and the scope of the invention as defined in the appended claims.

We claim:

1. A dental tool for use with an ultrasonic transducer, the tool comprising:
   a substantially elongate tool defined by a shaft having a proximal end with means for attachment to an ultrasonic transducer, and a distal end having a tip configured for performing a dental procedure;
   said distal end having a portion of straight cylindrical wall from said tip inward toward said proximal end; and
   a contra-angle between said cylindrical wall and said proximal end, wherein said shaft tapers from said cylindrical wall to said contra-angle.

2. The tool of claim 1, wherein said contra-angle is curved outward in a first direction from said axis at an angle of about fifteen to twenty-five degrees and curved outward in a second direction across said axis at about forty-five degrees to said axis.

3. The tool of claim 2, wherein said cylindrical portion is about ten to about twenty millimeters in length.

4. The tool of claim 3, wherein said distal end is formed with a concave tip.

5. The tool of claim 3, wherein said distal end is formed with a pointed tip.

6. The tool of claim 1, wherein said distal end is formed with a pointed tip.

7. The tool of claim 1, wherein said distal end is formed with a concave tip.

8. The tool of claim 1, wherein said cylindrical portion is about ten to about twenty millimeters in length.

9. The tool of claim 8, wherein said distal end is formed with a pointed tip.

10. The tool of claim 8, wherein the tool is is composed of stainless steel.

11. The tool of claim 10, wherein the tool is heat treated to about 40–42 Rockwell-C hardness prior to applying a metal nitride coating.

12. The tool of claim 11, wherein said distal end is formed with a concave tip.

13. The tool of claim 11, wherein said distal end is formed with a pointed tip.

14. The tool of claim 1, wherein said contra-angle is curved outward in a first direction from said axis at an angle of about fifteen to twenty-five degrees and curved outward in a second direction across said axis at about seventy degrees to said axis.

15. An ultrasonic dental tool for use in an ultrasonic transducer for root canal procedures, the tool comprising:
   an elongated tool defined by a shaft having a proximal end and a distal end, a threaded connection member on said proximal end for attachment to an ultrasonic transducer, and a tip configured for performing a dental procedure on said distal end, said shaft having a straight cylindrical portion of uniform diameter on said distal end from said tip inward toward said proximal end, a contra-angle portion of substantially uniform diameter adjacent said connection member at said proximal end, and a uniform gradual tapered portion intermediate said cylindrical portion at said distal end and said contra-angle portion at said proximal end.

16. The tool of claim 15, wherein the contra-angle portion is curved outward in a first direction from said axis at an angle of about fifteen degrees and curved outward in a second direction across said axis at about forty-five degrees to said axis.

17. The tool of claim 16, wherein said distal end is formed with a pointed tip.

18. The tool of claim 17, wherein said cylindrical portion is about ten to about twenty millimeters in length.

19. The tool of claim 17, wherein said cylindrical portion is about ten to about twenty millimeters in length.

20. The tool of claim 15, wherein said contra-angle is curved outward in a first direction from said axis at an angle of about fifteen to twenty-five degrees and curved outward in a second direction across said axis at about forty-five degrees to said axis.

21. The tool of claim 15, wherein said contra-angle is curved outward in a first direction from said axis at an angle of about fifteen to twenty-five degrees and curved outward in a second direction across said axis at about seventy degrees to said axis.

22. An ultrasonic dental tool for use in an ultrasonic transducer for root canal procedures, the tool comprising:

an elongated tool defined by an elongated shaft having a proximal end and a distal end, a threaded connector on said proximal end for attachment to an ultrasonic transducer, and a tip configured for performing a root canal dental procedure on said distal end, said shaft having an elongated straight cylindrical portion of uniform diameter and a length of from about 5 mm to about 12 mm on said distal end from said tip inward toward said proximal end, an elongated contra-angle portion of substantially uniform diameter adjacent said threaded connector on said proximal end curved outward in a first direction from said axis at an angle of about fifteen degrees and curved outward in a second direction across said axis at about forty-five degrees to said axis, and a uniform gradual tapered portion intermediate said cylindrical portion of said distal end and said contra-angle portion of said proximal end.

23. The tool of claim 22, wherein said cylindrical portion is about ten to about twenty millimeters in length.

24. The tool of claim 23, wherein said distal end is formed with a concave tip.

25. The tool of claim 24, wherein said distal end is formed with a pointed tip.

* * * * *